United States Patent
Kim et al.

(10) Patent No.: US 10,849,733 B2
(45) Date of Patent: Dec. 1, 2020

(54) GLUCOSE-RESPONSIVE ARTIFICIAL MUSCLE AND MANUFACTURING METHOD THEREFOR

(71) Applicant: INDUSTRY-UNIVERSITY COOPERATION FOUNDATION HANYANG UNIVERSITY, Seoul (KR)

(72) Inventors: Seon Jeong Kim, Seoul (KR); Sachan Ko, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 135 days.

(21) Appl. No.: 16/073,001

(22) PCT Filed: Jan. 26, 2017

(86) PCT No.: PCT/KR2017/000931
§ 371 (c)(1),
(2) Date: Jul. 26, 2018

(87) PCT Pub. No.: WO2017/131456
PCT Pub. Date: Aug. 3, 2017

(65) Prior Publication Data
US 2019/0029801 A1    Jan. 31, 2019

(30) Foreign Application Priority Data
Jan. 29, 2016    (KR) ........................ 10-2016-0011633

(51) Int. Cl.
B29C 64/00    (2017.01)
A61F 2/08    (2006.01)
(Continued)

(52) U.S. Cl.
CPC ................ A61F 2/08 (2013.01); B29C 70/44 (2013.01); C08B 37/0072 (2013.01); C08L 5/08 (2013.01);
(Continued)

(58) Field of Classification Search
CPC .......... A61F 2/08; C08B 37/0072; B82Y 5/00
(Continued)

(56) References Cited

U.S. PATENT DOCUMENTS 5,062,841 A     11/1991    Siegel
9,211,362 B2 *  12/2015    Hwang .................... A61F 2/08
(Continued)

FOREIGN PATENT DOCUMENTS

KR         10-1162039 B1       7/2012
KR      10-2015-0029318 A      3/2015
KR      10-2015-0092923 A      8/2015

OTHER PUBLICATIONS

Office Action issued in the Korean Patent Office in corresponding Korean Application No. 10-2016-0011633 (not attached).
(Continued)

Primary Examiner — Suzette J Gherbi
(74) Attorney, Agent, or Firm — Sughrue Mion, PLLC

(57) ABSTRACT

The present invention relates to a glucose-reactive artificial muscle, and more particularly, to a carbon nanotube, a hydrogel-based glucose-reactive artificial muscle which has a reversible volume change due to variations in glucose concentration, a method of forming the same, a rotary artificial muscle using the same, and a method of detecting glucose. The glucose-reactive artificial muscle according to the present invention may sense variations in glucose concentration with high sensitivity within a short time by providing reversible twisting using the swelling and shrinkage of hydrogels, which occur due to a change in internal (Continued)

anionic charges, caused by the bonding between a boronic acid introduced to the hydrogels and glucose.

8 Claims, 7 Drawing Sheets

(51) Int. Cl.
    *C08L 5/08*      (2006.01)
    *B29C 70/44*     (2006.01)
    *C08B 37/08*     (2006.01)
    *C08L 5/12*      (2006.01)
    *C08L 43/00*     (2006.01)
    *C08K 3/04*      (2006.01)
    *B82Y 5/00*      (2011.01)

(52) U.S. Cl.
    CPC .................. *C08L 5/12* (2013.01); *C08L 43/00* (2013.01); *A61F 2002/0894* (2013.01); *B82Y 5/00* (2013.01); *C08K 3/041* (2017.05)

(58) Field of Classification Search
    USPC ........................................ 424/423; 623/14.13
    See application file for complete search history.

(56) References Cited

U.S. PATENT DOCUMENTS

| | | | |
|---|---|---|---|
| 2004/0018226 A1* | 1/2004 | Wnek ................. | D01D 5/0038 |
| | | | 424/443 |
| 2010/0279421 A1 | 11/2010 | Strano et al. | |
| 2012/0004522 A1* | 1/2012 | Kim, III ............. | A61B 5/14735 |
| | | | 600/345 |
| 2012/0253464 A1* | 10/2012 | Hwang ................... | A61L 27/56 |
| | | | 623/13.18 |
| 2013/0287836 A1* | 10/2013 | Ingber .................... | A61L 27/48 |
| | | | 424/443 |
| 2015/0133752 A1 | 5/2015 | Iverson et al. | |
| 2015/0359886 A1* | 12/2015 | Wu .................... | A61K 41/0052 |
| | | | 604/500 |
| 2016/0199538 A1* | 7/2016 | Schussler ................ | A61L 31/16 |
| | | | 424/93.7 |
| 2016/0296665 A1* | 10/2016 | Ingber ..................... | A61L 27/54 |
| 2019/0160110 A1* | 5/2019 | Wei ......................... | A61L 27/54 |
| 2020/0088174 A1* | 3/2020 | Tawfick .................... | A61F 2/00 |
| 2020/0199199 A1* | 6/2020 | Lim ................. | C07K 14/43504 |

OTHER PUBLICATIONS

International Search Report of PCT/KR2017/000931 dated May 8, 2017 [PCT/ISA/210] English Translation.

* cited by examiner

[Fig 1]
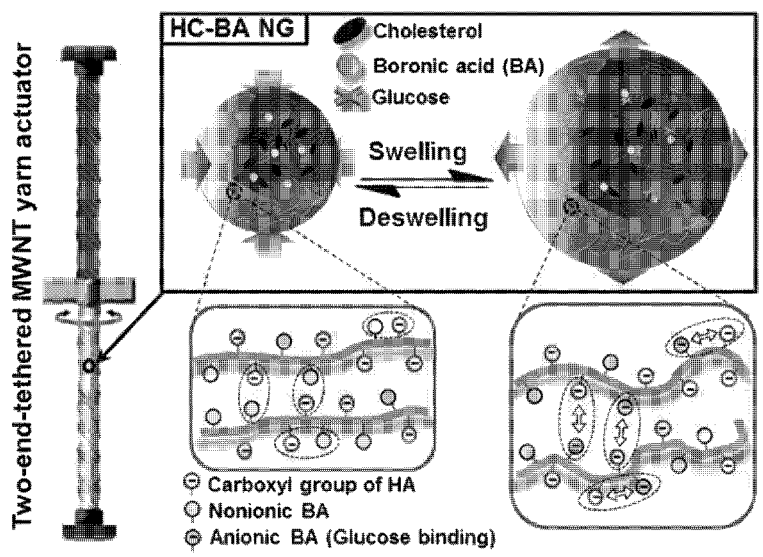
[Fig 2A]
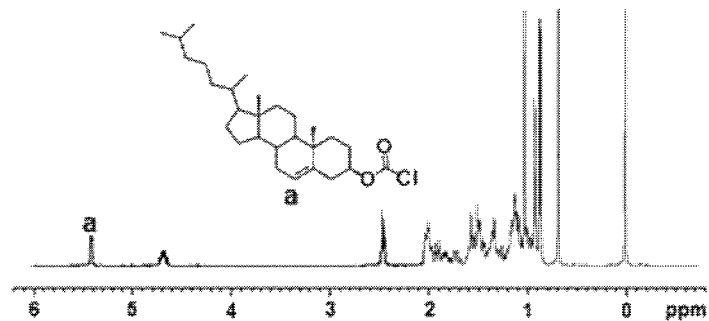
[Fig 2B]
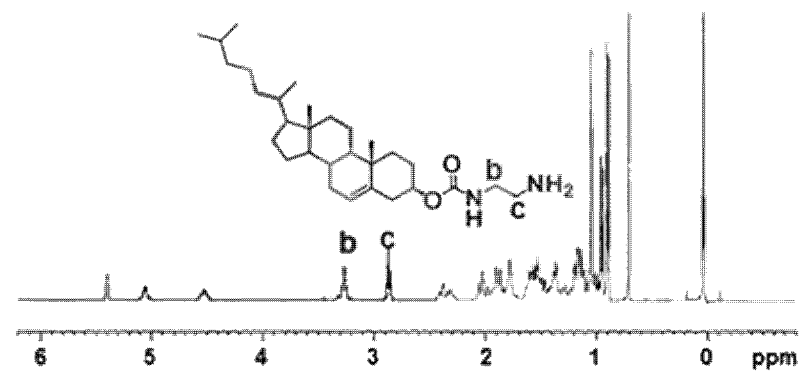

[Fig 2C]
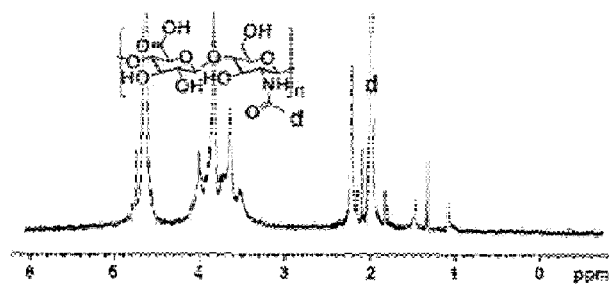
[Fig 2D]
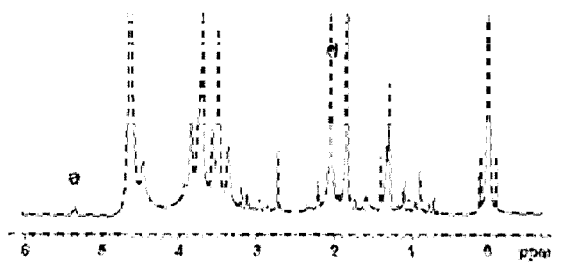
[Fig 3]
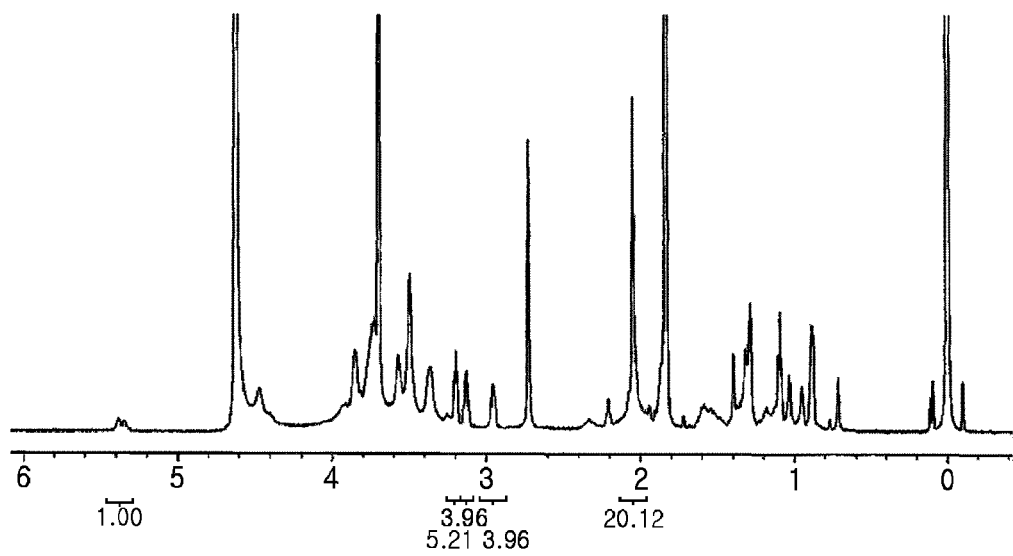

[Fig 4]
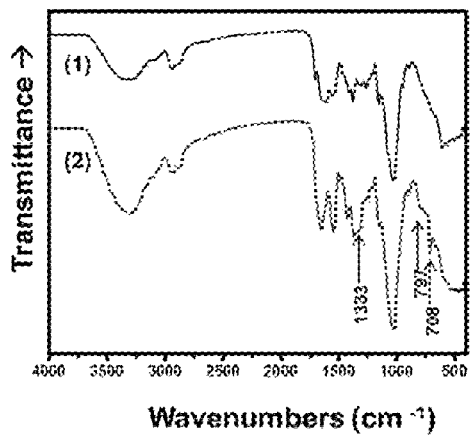
[Fig 5]
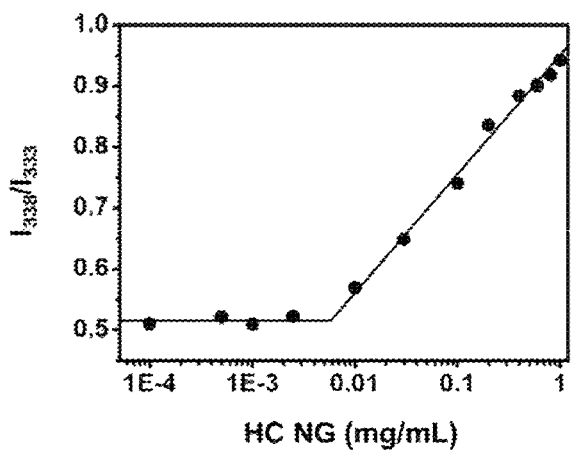
[Fig 6]
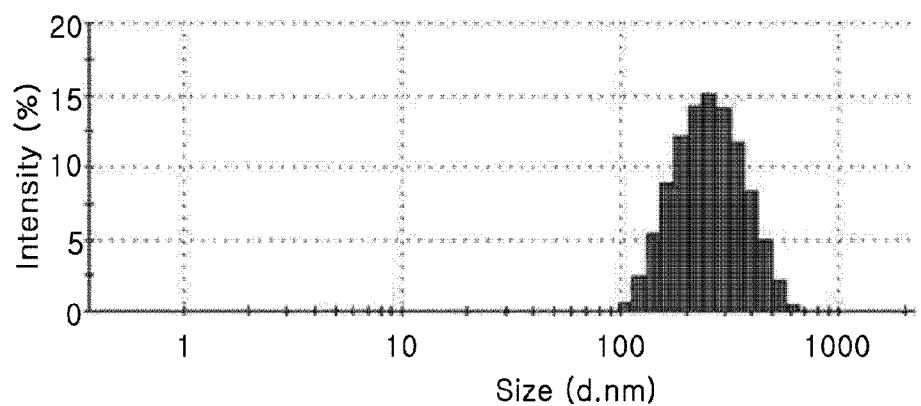

【Fig 7A】
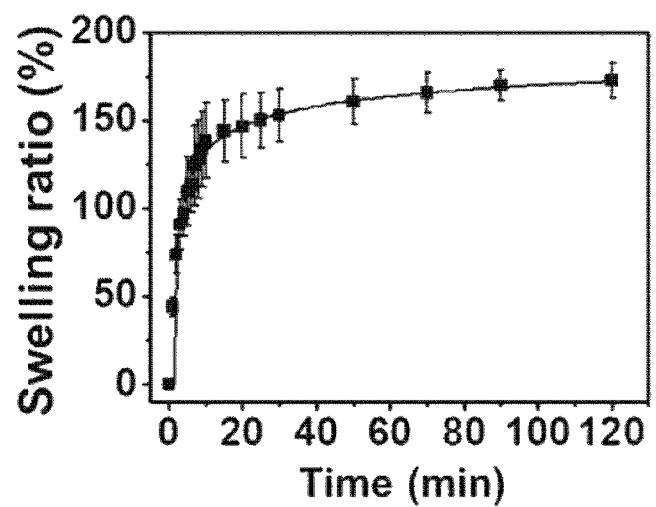
【Fig 7B】
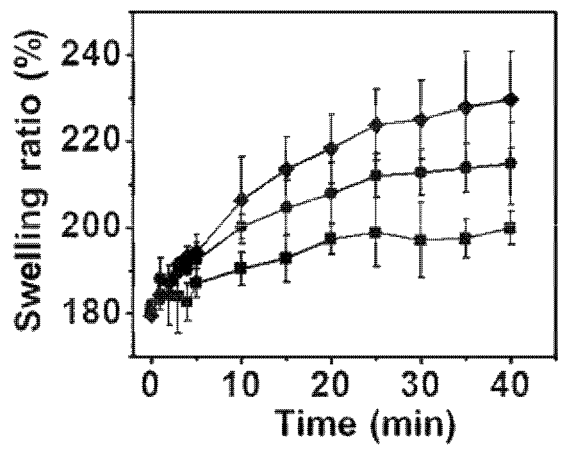

[Fig 7C]
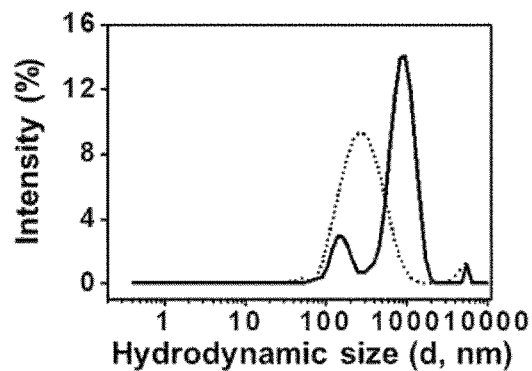
[Fig 7D]
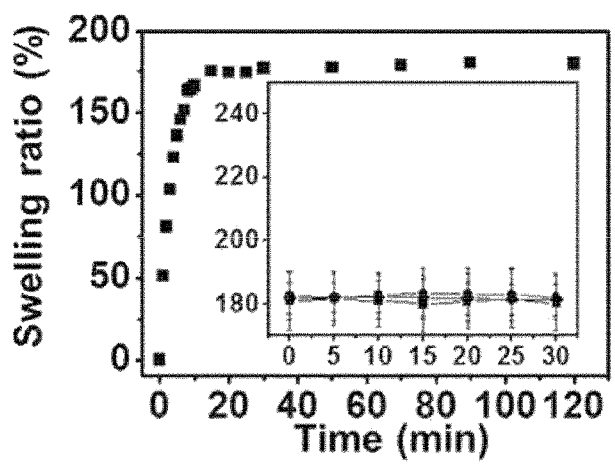
[Fig 8A]
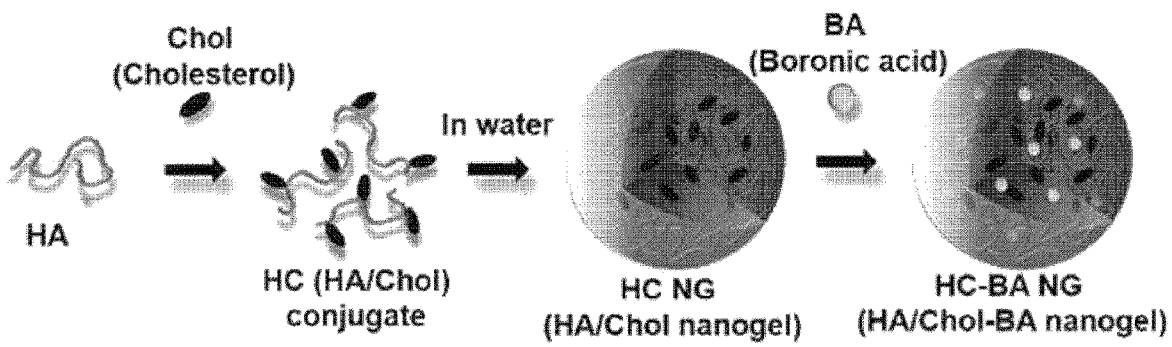

【Fig 8B】
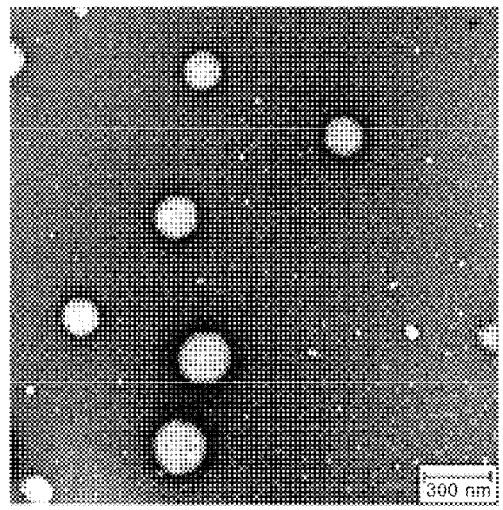
【Fig 8C】
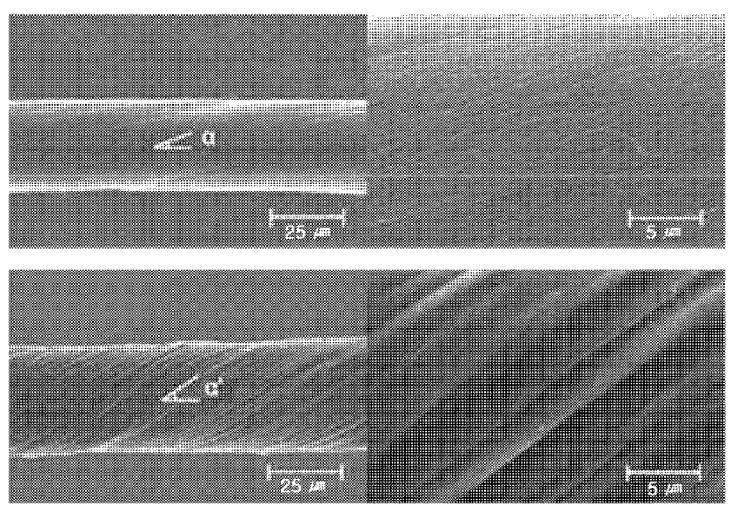

[Fig 9]
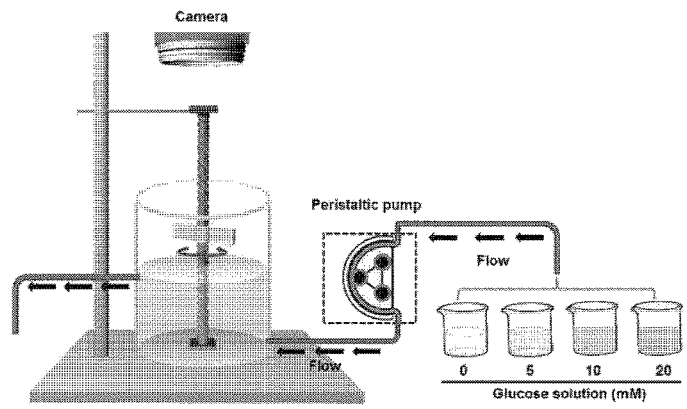
[Fig 10A]
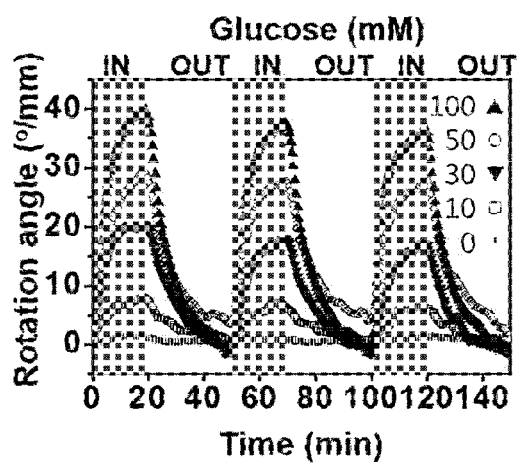
[Fig 10B]
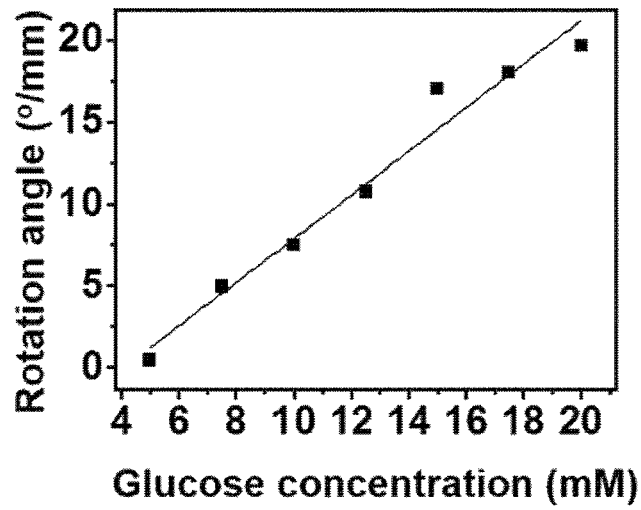

GLUCOSE-RESPONSIVE ARTIFICIAL MUSCLE AND MANUFACTURING METHOD THEREFOR

CROSS REFERENCE TO RELATED APPLICATIONS

This application is a National Stage of International Application No. PCT/KR2017/000931, filed Jan. 26, 2017, claiming priority based on Korean Patent Application No. 10-2016-0011633, filed Jan. 29, 2016.

TECHNICAL FIELD

The present invention relates to a glucose-reactive artificial muscle, and more particularly, to a glucose-reactive artificial muscle which consists of carbon nanotubes (CNTs) and a hydrogel having a reversible volume change according to variations in glucose concentration, a method of forming the same, a rotary artificial muscle using the same, and a method of detecting glucose.

BACKGROUND ART

Glucose monitoring is a very important factor in determining the optimal treatment for diabetic patients resulting from insulin deficiency (W. L. Clarke, D. Cox, L. A. Gonder-Frederick, W. Carter, S. L. Pohl, *Diabetes Care* 1987, 10, 622.). For this reason, continuous glucose monitoring techniques using various glucose-sensitive materials have been reported (R. Ballerstadt, R. Ehwald, *Biosens. Bioelectron.* 1994, 9, 557., D. C. Klonoff, *Diabetes Care* 2005, 28, 1231., W. Yan, X. Feng, X. Chen, W. Hou, J.-J. Zhu, *Biosens. Bioelectron.* 2008, 23, 925.). Among these techniques, glucose oxidase (GOx)-based sensors show very impressive results, but have disadvantages such as high sensitivity of the enzyme to environmental change, the requirement of oxygen or a redox mediator, the generation of hydrogen peroxide after glucose consumption, etc. (A. S. G. Huggett, D. A. Nixon, *Lancet* 1957, 2, 368., J. Wang, *Chem. Rev.* 2008, 108, 814.).

Accordingly, in recent years, a boronic acid reversibly bonded with glucose, which is a non-enzymatic glucose-sensing material, has attracted attention as a novel alternative to glucose sensors (J. P. Lorand, J. O. Edwards, *J. Org. Chem.* 1959, 24, 769., A. Kikuchi, K. Suzuki, O. Okabayashi, H. Hoshino, K. Kataoka, Y. Sakurai, T. Okano, *Anal. Chem.* 1996, 68, 823.). However, glucose-sensing techniques using a boronic acid have problems such as the limitation in detection using fluorescent probes, low in vivo stability, the requirement of an external energy source, etc., which must be overcome (V. L. Alexeev, S. Das, D. N. Finegold, S. A. Asher, *Clin. Chem.* 2004, 50, 2353., C. Zhang, G. G. Cano, P. V. Braun, *Adv. Mater.* 2014, 26, 5678.).

Meanwhile, hyaluronic acid (HA), which is a linear, anionic glycosaminoglycan having D-glucuronic acid and D-N-acetylglucosamine as repeat units, is widely distributed in the extracellular matrix and known to be involved in structural and biological functions due to its ability to interact with other materials (T. C. Laurent, J. R. E. Fraser, *Faseb J.* 1992, 6, 2397., L. Lapcik, S. De Smedt, J. Demeester, P. Chabrecek, *Chem. Rev.* 1998, 98, 2663.). Unlike other synthetic polymers, HA is a biocompatible, biodegradable and non-immunogenic material, and thus has been widely studied in biomedical and pharmaceutical applications (N. Itano, F. Atsumi, T. Sawai, Y. Yamada, O. Miyaishi, T. Senga, M. Hamaguchi, K. Kimata, *Proc. Natl. Acad. Sci. U.S.A.* 2002, 99, 3609., V. Trochon, C. Mabilat, P. Bertrand, Y. Legrand, F. SmadjaJoffe, C. Soria, B. Delpech, H. Lu, *Int. J. Cancer* 1996, 66, 664., J. B. Leach, K. A. Bivens, C. W. Patrick, C. E. Schmidt, *Biotechnol. Bioeng.* 2003, 82, 578.). Recently, various polymer nanoparticles or nanogels using HA had been synthesized and used as drug delivery systems and bio imaging probes (J. A. Burdick, G. D. Prestwich, *Adv. Mater.* 2011, 23, H41., K. Y. Choi, H. Chung, K. H. Min, H. Y. Yoon, K. Kim, J. H. Park, I. C. Kwon, S. Y. Jeong, *Biomaterials* 2010, 31, 106.), but there were no studies on the application of HA as a biosensor.

Meanwhile, due to high electric conductivity, excellent mechanical strength, large surface area, etc., a CNT sheet and a CNT yarn are receiving much attention in various applications such as a supercapacitor, an actuator for an artificial muscle and an ultra-light weight electromagnetic shielding material. Particularly, a multi-wall CNT yarn containing a guest material has been focused on research of physicochemical applications such as a superconductor, a material for a lithium ion battery, a graphene ribbon, a catalyst nanofiber for a fuel cell, a photocatalyst, etc. (A. B. Dalton, S. Collins, E. Munoz, J. M. Razal, V. H. Ebron, J. P. Ferraris, J. N. Coleman, B. G. Kim, R. H. Baughman, *Nature* 2003, 423, 703., M. D. Lima, S. Fang, X. Lepro, C. Lewis, R. Ovalle-Robles, J. Carretero-Gonzalez, E. Castillo-Martinez, M. E. Kozlov, J. Oh, N. Rawat, C. S. Haines, M. H. Hague, V. Aare, S. Stoughton, A. A. Zakhidov, R. H. Baughman, *Science* 2011, 331, 51.), but until now, there have been no reports on the application of a multi-wall CNT yarn as a material that is driven in response to external factors such as pH, ionic strength, an antigen, an enzyme, a biomolecule, etc.

DISCLOSURE

Technical Problem

The present invention is provided to resolve the above-mentioned problems, and thus provides a glucose-reactive artificial muscle which is driven by variations in glucose concentration using a hydrogel having a reversible volume change through a reaction with glucose and a CNT fiber, and a method of forming the same.

Technical Solution

To solve the above-mentioned problem of the present invention, the present invention provides a glucose-reactive hydrogel-based artificial muscle, which includes a multi-layered CNT sheet; and hydrogels embedded in the surface of the CNT sheet. The artificial muscle is a fiber type, which is formed by twisting the hydrogel-embedded CNT sheet, and the hydrogels have reversible volume changes through a reaction with glucose.

According to the present invention, the artificial muscle may have twisted or coiled structure.

According to the present invention, the hydrogel may be boronic acid-conjugated hyaluronic acid/cholesterol nanogels, represented by Formula 1 below:

[Formula 1]

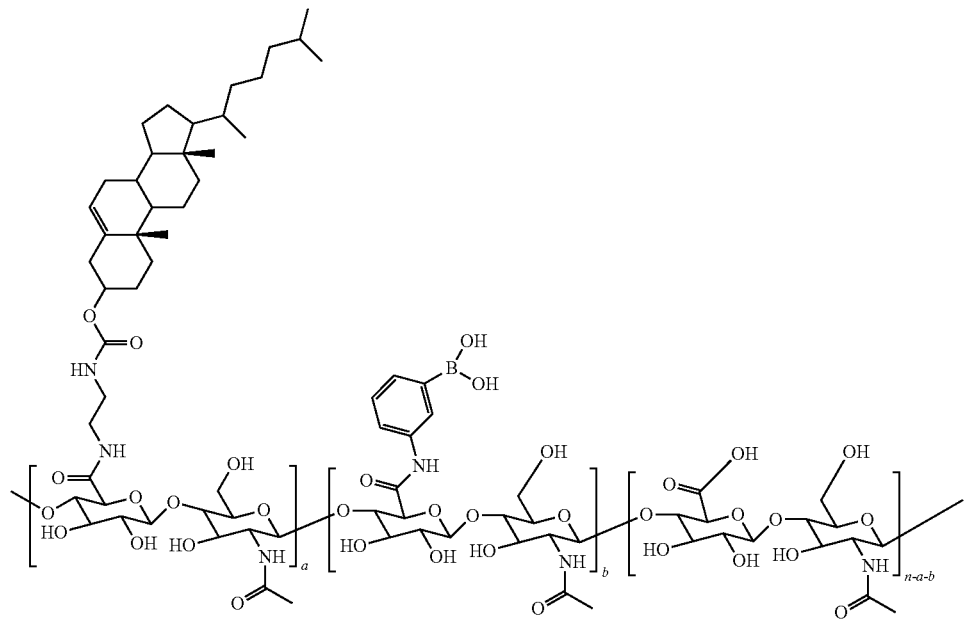

wherein n is an integer of 2 to 20000, and each of a and b is an integer of 1 to 10000.

According to the present invention, the hydrogels may be embedded at a content of 80 to 99 wt % with respect to the total content of the hydrogel-embedded CNT sheet.

According to the present invention, the glucose concentration may range from 1 to 100 mM.

In addition, to solve the above-mentioned problem, the present invention provides a method of forming a glucose-reactive hydrogel-based artificial muscle, which includes (a) embedding hydrogels in the surface of a multi-layered CNT sheet; and (b) twisting the hydrogel-embedded CNT sheet to be processed into a fiber type, and the hydrogels have reversible volume changes by the reaction with glucose.

Here, the structure of the artificial muscle, the formula and content of hydrogels, and a glucose concentration are the same as defined above.

In addition, to solve the above-mentioned problem, the present invention provides a glucose-reactive, rotary artificial muscle, which includes a fiber-type artificial muscle unit including the glucose-reactive hydrogel-based artificial muscle according to any one of claims 1 to 5; and a fiber-type scaffold unit formed by twisting a multi-layered CNT sheet, in which one end of the fiber-type artificial muscle unit is connected with one end of the fiber-type scaffold unit by a paddle, and the other end of the fiber-type artificial muscle unit and the other end of the fiber-type scaffold unit are each independently fixed using fixing devices.

According to the present invention, the fiber-type artificial muscle unit and the fiber-type scaffold unit may be twisted in the same twisting direction so as to have a twisted or coiled structure.

The hydrogels included in the fiber-type artificial muscle unit are expanded or shrunk in volume by the reaction with glucose, and the other end of the fiber-type artificial muscle unit and the other end of the fiber-type scaffold unit are each independently fixed using fixing devices. When the hydrogels are swelled, the twisting of the fiber-type artificial muscle unit becomes loose and thus is rotated in an untwisting direction, and therefore the fiber-type scaffold unit connected to the fiber-type artificial muscle unit obtains a rotary force. On the other hand, when the hydrogel is shrunk, the fiber-type artificial muscle unit is twisted with a higher twist number, and therefore the fiber-type scaffold unit connected to the fiber-type artificial muscle unit obtains a rotary force in an opposite direction due to the twisting.

The rotary force of the fiber-type scaffold unit may act as a driving force that allows the artificial muscle to be more rapidly and easily driven.

In addition, to solve the above-mentioned problem, the present invention provides a method of detecting glucose, which includes in vivo implanting the glucose-reactive, rotary artificial muscle according to claim 11; and measuring the movement of the glucose-reactive, rotary artificial muscle in vivo implanted.

According to the present invention, the glucose concentration may range from 1 to 100 mM.

Advantageous Effects

A glucose-reactive artificial muscle according to the present invention can sense variations in glucose concentration with high sensitivity within a short time by providing reversible twisting using the swelling and shrinkage of hydrogels, which occur due to a change in internal anionic charges, caused by the bonding between a boronic acid introduced to the hydrogels and glucose. Accordingly, the present invention can be effectively applied to a variety of medical devices including drug delivery systems, BioMems, bio nano- and micro-machines, smart scaffolds for tissue engineering, drug injection channel opening/closing devices that are regulated according to blood sugar, drug injection concentration regulatory devices, nerve stimulators, etc., and nanomedical, drug delivery, rehabilitation medical and bioengineering fields.

DESCRIPTION OF DRAWINGS

FIG. 1 illustrates a glucose-reactive, rotary, artificial muscle according to the present invention and a driving principle thereof.

FIG. 2 illustrates the $^1$H NMR spectra of materials used in hydrogel synthesis of the present invention, in which (A) is the $^1$H NMR spectrum of cholesteryl chloroformate, (B) is the $^1$H NMR spectrum of cholesterol-$NH_2$, (C) is the $^1$H NMR spectrum of Hyaluronic acid(HA), and (D) is the $^1$H NMR spectrum of Hyaluronic acid nanogel(HC NC).

FIG. 3 illustrates the $^1$H NMR spectrum of a HA hydrogel used in hydrogel synthesis of the present invention.

FIG. 4 illustrates the FT-IR spectrum results of HC NG and HC-BA NG, which are used in the present invention.

FIG. 5 is a graph illustrating the change in $I_{338}/I_{333}$ plot according to the concentration of HC NG, and a critical micelle concentration (CMC) of the HC NG is calculated to be approximately 0.006 mg/ml.

FIG. 6 is a graph illustrating particle sizes of HC NG analyzed through dynamic light scattering.

FIG. 7 is a graph illustrating swelling characteristics of hydrogels of the present invention, in which (A) illustrates the swelling characteristic of an HC-BA NG pellet over time in PBS buffer, (B) illustrates the swelling characteristic of the HC-BA NG pellet over time at various glucose concentrations (20 mM (♦), 10 mM (●) and 5 mM (■)), (C) illustrates a fluid dynamic size of HC-BA NG in PBS buffer measured by dynamic light scattering in the presence (solid line) or absence (dotted line) of 100 mM glucose, and (D) illustrates the swelling characteristic (inserted graph, control) of HC NG in PBS buffer in the presence of glucose.

FIG. 8 illustrates a process of forming HC-BA NG (A), a TEM image of HC-BA NG (B), and SEM images (left: low magnification, and right: high magnification) of a fiber-type scaffold unit (neat MWNT yarn; top) and a fiber-type artificial muscle unit (HC-BA NG-coated yarn)(C).

FIG. 9 illustrates a system for measuring a driving characteristic according to a glucose concentration of a glucose-reactive, rotary, artificial muscle according to the present invention.

FIG. 10A illustrates a reversible twisting characteristic according to glucose sensing of a multi-wall CNT yarn according to the present invention, and FIG. 10B illustrates a paddle rotation angle according to a glucose concentration.

MODES OF THE INVENTION

Hereinafter, the present invention will be described in detail.

To overcome disadvantages of a conventional glucose oxidase-based glucose monitoring technique, the present invention is directed to providing an artificial muscle that may sense variations in glucose concentration with high sensitivity within a short time by applying hydrogels prepared using a boronic acid which is a non-enzymatic glucose sensing material and HA which is widely used in the synthesis of a nanogel to a CNT yarn-based artificial muscle.

To this end, the present invention provides a glucose-reactive hydrogel-based artificial muscle, which includes a multi-layered CNT sheet; and hydrogels embedded in the surface of the CNT sheet. In this case, the artificial muscle is a fiber type, which is formed by twisting the hydrogel-embedded CNT sheet, and the hydrogels have reversible volume changes through a reaction with glucose.

Here, the artificial muscle may be formed through a process of twisting the hydrogel-embedded CNT sheet, and thereby may have a twisted or coiled structure. In addition, when the hydrogels may be swelled due to the reaction with glucose, the artificial muscle may rotate in an untwisting direction so as to be less twisted or coiled, or when a glucose concentration is reduced, due to shrinkage of the hydrogels, the artificial muscle may be rotated in a twisted direction and thus may be more twisted or coiled.

Here, the twisted structure means a helically-twisted structure, and the coiled structure means a spring- or coil-like structure. Specifically, a difference between the twisted structure and the coiled structure is determined by a twist number (turns/m) according to the diameter of a CNT yarn formed by twisting the hydrogel-embedded CNT sheet. For example, when the twist number ranges from 1000 to 4000 turn/m, the twisted structure is formed, and when the twist number ranges from 4000 to 8000 turn/m, the coiled structure is formed.

Specifically, as the artificial muscle is formed in a twisted or coiled structure, the hydrogels included in the artificial muscle are swelled with high efficiency, resulting in a longitudinal change in the artificial muscle, that is, a change into mechanical energy. Therefore, the above-described artificial muscle having a twisted or coiled structure has a reversible characteristic in that it is extended due to the swelling of the hydrogels when coming into contact with glucose, and it is shrunk to an initial state as much as it is swelled when the contact with glucose disappears.

When the artificial muscle is formed by twisting the hydrogel-embedded CNT sheet, if it has excellent elasticity and flexibility, it may have any one of a variety of structures, which is selected from an Archimedean structure, a dual Archimedean structure and a Fermat structure.

The hydrogels may be boronic acid-conjugated hyaluronic acid/cholesterol nanogels (HC-BA NGs) represented by Formula 1 below:

[Formula 1]

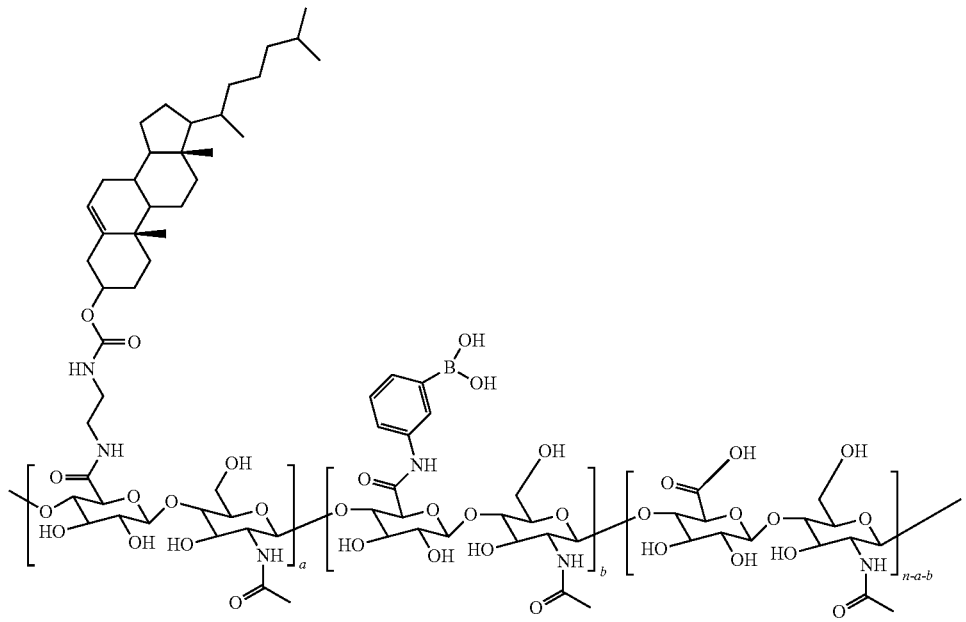

In Formula 1, n is an integer of 2 to 20000, and each of a and b is an integer of 1 to 10000.

The hydrogels are HC-BA NGs as shown in Formula 1, and when, in the presence of glucose, a boronic acid is bonded with glucose, the boronic acid exhibits a negative charge, and therefore, the hydrogels are swelled due to electrostatic repulsion with a carboxyl group of HA, which exhibits a negative charge. On the other hand, when a glucose concentration is reduced, or under a glucose-reducing condition, an amount of boronic acid that fails to be bonded with glucose is increased, overall negative charges of the hydrogel nanoparticles are reduced and thus the electrostatic repulsion disappears, resulting in shrinkage of the hydrogel. Here, since the swelling and shrinking characteristics of the hydrogels are reversible as can be seen from the results of the following examples, the present invention is meaningful in that it suggests the probability of an artificial muscle as a biosensing application through the twisting of the artificial muscle, induced by a volume change of the hydrogel.

The relative content of each component constituting the artificial muscle according to the present invention, such as a CNT sheet or hydrogels, is an important factor in glucose sensitivity or the driving characteristics of the artificial muscle, and thus the hydrogels may be included at a content of 80 to 99 wt % with respect to the total content of the hydrogel-embedded CNT sheet. When the hydrogel content is less than the lower limit value, the sensitivity of the artificial muscle to glucose is decreased, or when the hydrogel content is more than the higher limit value, the mechanical strength is lowered and the glucose concentration-dependent swelling ratio of the artificial muscle is not increased, compared with the increased hydrogel content.

In addition, as seen from the results of the following examples, the artificial muscle according to the present invention may sense glucose at a low concentration ranging from 1 to 100 mM with high sensitivity.

Meanwhile, the present invention provides a method of forming a glucose-reactive hydrogel-based artificial muscle, which includes: (a) embedding hydrogels in the surface of a multi-layered CNT sheet; and (b) twisting the hydrogel-embedded CNT sheet to be processed into a fiber type, and the hydrogels have a reversible volume change which results from the reaction with glucose.

Here, the structure of the artificial muscle, the formula and content of hydrogels, and a glucose concentration are the same as defined above.

The CNT sheet may be prepared by directly purchasing a planar or multi-layered-planar-type porous CNT sheet, or by drawing from a CNT forest. Since the CNT sheet prepared as described above has a planar structure and includes an empty space between CNT fibers constituting the CNT sheet, it has a large surface for bonding with the hydrogels.

In addition, to uniformly embed the hydrogels in the CNT sheet, the CNT sheet is fixed at both ends in advance while the planar structure is maintained, and for example, the CNT sheet may be fixed onto a slide glass.

Subsequently, the CNT sheet is immersed in a hydrogel-containing solution and then dried so as to embed the hydrogels in the surface of each CNT sheet.

Afterward, the hydrogel-embedded CNT sheet is twisted and processed into a fiber type. Here, the twist number (turn/m) of the CNT sheet may range, but is not specifically limited to, for example, from 1000 to 5000, and the artificial muscle formed through such a twisting manner may have a diameter of 20 to 70 μm. According to the use of the artificial muscle, the twist number may be adjusted.

The artificial muscle formed according to the present invention may have a change in the volume of a hydrogel when reacting with glucose as described above, thereby being reversibly driven since a scaffold is bent, twisted or coiled due to the volume change of the hydrogel, and can bent, knotted, twisted or weaved due to excellent flexibility and a high tensile strength.

In addition, the present invention provides a glucose-reactive, rotary, artificial muscle, which includes: a fiber-type artificial muscle unit including the glucose-reactive hydrogel-based artificial muscle; and a fiber-type scaffold unit formed by twisting a multi-layered CNT sheet. One end of the fiber-type artificial muscle unit is connected with one end of the fiber-type scaffold unit using a paddle, and the other end of the fiber-type artificial muscle unit and the other end of the fiber-type scaffold unit may be each independently fixed using fixing devices.

Here, the structure of the artificial muscle, the formula and content of hydrogels, and a glucose concentration are the same as defined above.

According to the present invention, the hydrogels included in the fiber-type artificial muscle unit may react with glucose and thus may be swelled or shrunk so as to have a volume change, and since one end of the fiber-type artificial muscle unit and one end of the fiber-type scaffold unit are each independently fixed using fixing devices, when the hydrogels are swelled, the twisting of the fiber-type artificial muscle unit becomes loose and thus is rotated in an untwisting direction, and therefore the fiber-type scaffold unit connected to the fiber-type artificial muscle unit obtains a rotary force. On the other hand, when the hydrogel is shrunk, the fiber-type artificial muscle unit is twisted with a higher twist number, and therefore the fiber-type scaffold unit connected to the fiber-type artificial muscle unit obtains a rotary force in an opposite direction due to the twisting.

In this case, when the fiber-type artificial muscle unit and the fiber-type scaffold unit have opposite twisting directions, both of the upper and lower portions are rotated in reverse directions due to the swelling of the hydrogels in the lower portion, but when the hydrogels in the lower portion are shrunk, both upper and lower portions are rotated in the twisting direction, thereby increasing a degree of twisting, but it may be difficult to have reversible rotation. Accordingly, the fiber-type artificial muscle unit and the fiber-type scaffold unit may be twisted in the same twisting direction so as to have a twisted or coiled structure.

The rotary force of the fiber-type scaffold unit may act as an energy source for reversibly swelling or shrinking the fiber-type artificial muscle unit in the lower portion, and therefore the artificial muscle may be driven more rapidly and easily, and repeated reversible movements may be achieved.

Specifically, the glucose-reactive, rotary, artificial muscle is shown in FIG. 1. Referring to FIG. 1, the upper portion consisting of a fiber-type scaffold unit is connected with the lower portion consisting of a fiber-type artificial muscle unit using a paddle. In addition, each end of the fiber-type scaffold unit and the fiber-type artificial muscle unit is fixed using a fixing device.

The fixing device may consist of an aqueous solution, an electrolyte and a material having in vivo stability, for example, epoxy, but the present invention is not specifically limited thereto.

The glucose-reactive artificial muscle according to the present invention may be used for diagnosis of a disease through sensing of the variations in glucose concentration due to the hydrogel characteristic of changing a volume through the reaction with glucose as described above.

Accordingly, the present invention provides a method of detecting glucose, which includes: in vivo implanting the glucose-reactive, rotary, artificial muscle; and measuring the movement of the glucose-reactive, rotary, artificial muscle implanted in vivo.

Hereinafter, the present invention will be described in further detail with reference to exemplary examples. However, these examples are provided to more specifically explain the present invention, and it will be apparent to those of skill in the art that the scope of the present invention is not limited to the examples.

Preparation Example 1. Preparation of HC-BA NGs

As hydrogels used in the present invention, HC-BA NGs having a reversible volume change through the reaction with glucose were synthesized according to the following reaction scheme, and a specific preparation method will be described as below.

[Reaction Scheme]

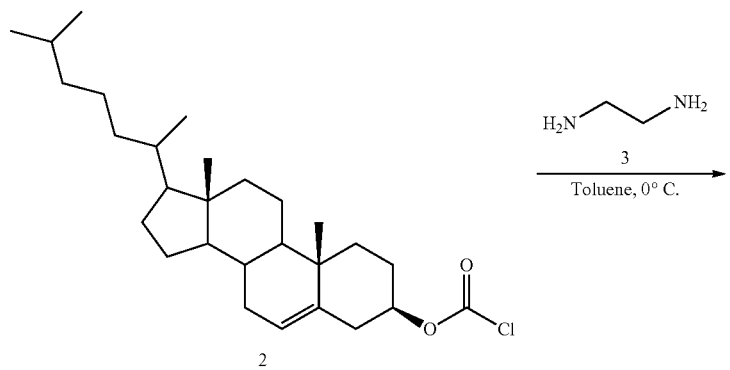

2

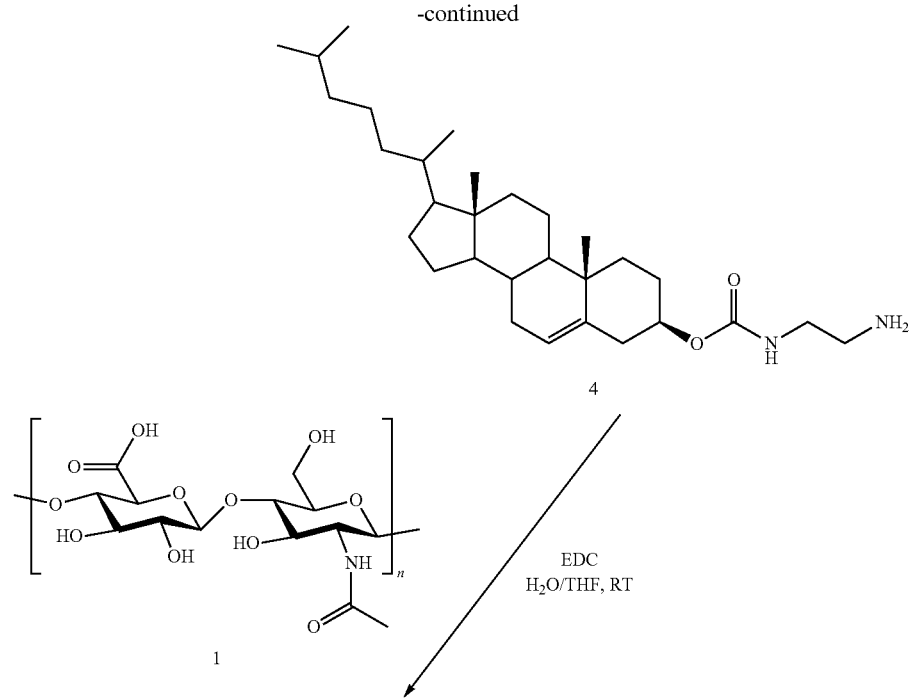
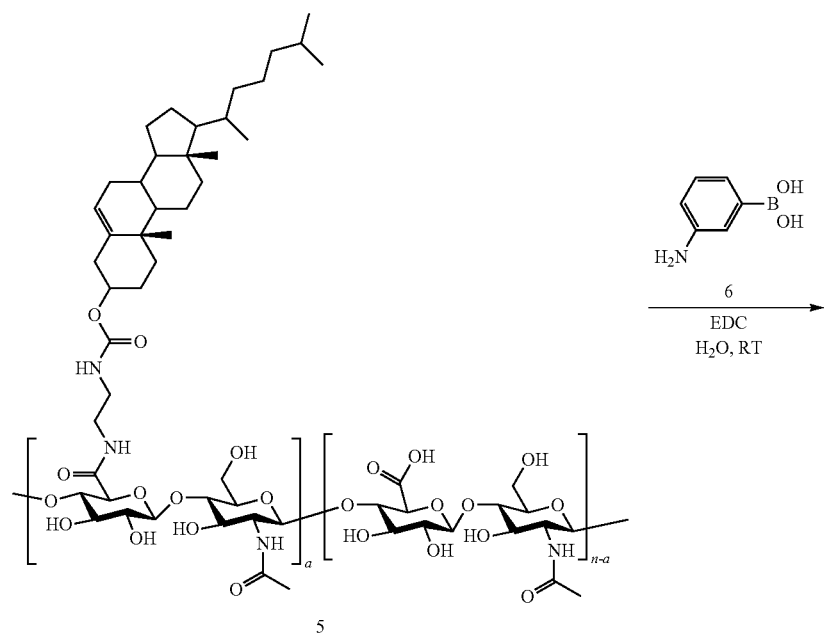

-continued

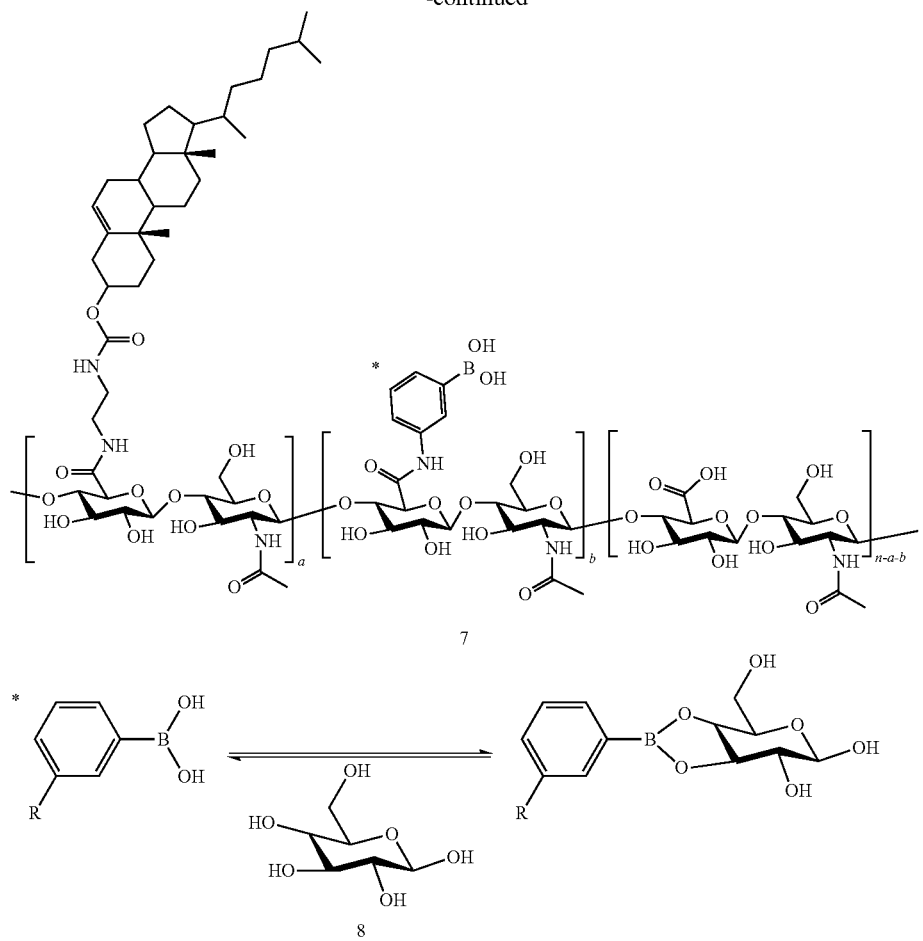

7

8

In the reaction scheme, the "1" represents HA, the "2" represents cholesteryl chloroformate, the "3" represents ethylenediamine, the "4" represents amine-modified cholesterol (cholesterol-$NH_2$), the "5" represents a HA/cholesterol nanogel (HC NG), the "6" represents 3-aminophenylboronic acid, the "7" represents HC-BA NG, the "8" represents a reversible bonding between phenylboronic acid and glucose, and in this reaction scheme, n is an integer of 2 to 20000, and each of a and b is an integer of 1 to 10000.

(1) Materials

Sodium hyaluronate (HA200K, MW 213 kDa) was obtained from Lifecore Biomedical (Chaska, Minn., USA). Cholesterol chloroformate, ethylenediamine, N-(3-dimethylaminopropyl)-N'-ethylcarbodiimide (EDC), N-hydroxysulfosuccinimide (sulfo-NHS), 3-aminophenylboronic acid hydrochloride, and D-(+)-glucose were purchased from Sigma-Aldrich (St. Louis, Mo., USA).

(2) Synthesis of Cholesterol-$NH_2$

To prepare cholesterol-$NH_2$, cholesteryl chloroformate was reacted with ethylenediamine. Specifically, cholesteryl chloroformate (2.25 g, 5 mmol) in anhydrous toluene (50 mL) was added dropwise to a solution of ethylenediamine (16.7 mL, 250 mmol) in 150 mL of toluene at 0° C. for 10 minutes. After stirring overnight at room temperature, unreacted ethylenediamine was washed with distilled water, and the reaction mixture was dried with anhydrous magnesium sulfate. After the solvent was evaporated, the dried mixture was dissolved in a dichloromethane/methanol (1/1, v/v) solution, and a by-product was removed using a syringe filter (1 mm MWCO, PTFE, Whatman, N.J., USA). And then, the filtrate was crystalized by rotary evaporation, thereby obtaining cholesterol-$NH_2$.

(3) Synthesis of HA/Cholesterol Nanogels (HC NGs)

Cholesterol-$NH_2$ was bonded with a carboxyl group of HA by an EDC coupling method. Specifically, HA (100 mg, 244 mmol) was dissolved in 10 mL of distilled water. Then, EDC (93.5 mg) and sulfo-NHS (106 mg) were added to the resulting solution to activate the carboxyl group of HA for 30 minutes. Afterward, cholesterol-$NH_2$ (48.8 mmol) in 10 mL of tetrahydrofuran (THF) was slowly added dropwise to the HA solution and stirred so as to allow a reaction for 18 hours. After the reaction, the sample was dialyzed in a distilled water/THF (1/1, v/v) solution for 2 days and then in fresh water for 1 day using a cellulose membrane tube (MWCO 12 kDa, Spectrum Laboratories, Inc., CA, USA), and lyophilized, thereby preparing HC NGs.

(4) Preparation of HC-BA NGs

The synthesized HC NGs were reacted with 3-aminophenylboronic acid hydrochloride. Specifically, the crystallized HC NGs (20 mg) were resuspended in 10 mL of distilled water, and 10 mg of EDC was added to the solution and vigorously stirred. Then, 1 mL (50 mM) of 3-aminophenylboronic acid hydrochloride (in distilled water) was directly added dropwise to allow a reaction for 12 hours. The synthesized HC-BA was purified by dialysis, and recrystallized by lyophilization, thereby preparing HC-BA NGs.

Preparation Example 2. Formation of Glucose-Reactive Hydrogel-Based Artificial Muscle A multi-wall CNT (MWCNT) sheet consisting of three layers was formed using a method of drawing from a side wall of an MWCNT forest.

A HC-BA NG-embedded CNT sheet was formed by attaching the MWCNT sheet formed above to a slide glass, fixing both ends of the CNT sheet, immersing the slide glass in a 20% HC-BA NG solution for 30 seconds, and then drying the slide glass at room temperature.

Subsequently, a fiber-type, glucose-reactive hydrogel-based artificial muscle according to the present invention was formed by rewetting the HC-BA NG-embedded CNT sheet, attaching one end of the sheet to a motor, and twisting the sheet to have a chiral Z- or S-type structure by applying a twist number of 2100 turns/m to the left or right using a biscrolling method.

Here, the difference between a twisting structure and a coiled structure may be determined by a twist number (turns/m) applied according to the diameter of a fiber.

Preparation Example 3. Formation of Glucose-Reactive, Rotary Artificial Muscle A CNT yarn (bare MWCNT yarn) was formed by twisting only a CNT sheet. As shown in FIG. 1, the bare MWCNT yarn and the glucose-reactive hydrogel-based artificial muscle formed by twisting the CNT sheet into a fiber type in Preparation Example 2 were connected with a paddle having a size of 0.5×2.0 mm and then fixed, each of the ends, which were not connected with the paddle, of the CNT yarn and the glucose-reactive hydrogel-based artificial muscle was fixed using a waterproof epoxy adhesive, and after overnight drying, a glucose-reactive, rotary artificial muscle according to the present invention was formed.

Experimental Example

First, characteristics of the hydrogel used in the present invention were analyzed. The chemical structures and degrees of substitution of the HC NG and the HC-BA NG were defined by the number of bonded cholesterols per 100 β-glucosamine residues of HA, which was analyzed by $^1$H-NMR. It was confirmed that the cholesteryl chloroformate shows a characteristic double bond signal at 5.4 ppm (1H, —CHCH$_2$—)(FIG. 2A), and an ethylenediamine-reactive cholesterol showed specific peaks at 2.8 ppm (2H, —NH$_2$CH$_2$) and 3.2 ppm (2H, —NHCH$_2$—)(FIG. 2B). In the case of the HA, it was confirmed that the chemical shift of an N-acetyl group (d=2 ppm, 3H, —COCH$_3$)(FIG. 2C) was assigned to a specific peak. After the reaction between HA and the ethylenediamine-bonded cholesterol was ended, it was confirmed that the specific peak (d=5.4 ppm) of the cholesterol was present in a HC NG $^1$H NMR spectrum (FIG. 2). Afterward, the degree of substitution was measured from an integration ratio between the cholesterol peak (d=5.4 ppm) and the peak (d=2 ppm) of the N-acetyl group of the HA. When the reaction rate of the cholesterol-NH$_2$ group bonded with the carboxyl group of the HA was 0.2, the degree of substitution of the HC NG was determined to 14.9 mole % (FIG. 3). It was confirmed that the HC NG had reacted with 3-aminophenylboronic acid, and a phenylboronic acid residue in the HC-BA NG was clearly identified by FT-IR analysis (FIG. 4).

A CMC of the HC NG was measured in the presence of a pyrene fluorescence probe. Specifically, pyrene (30 mM) in acetone was diluted with distilled water to 1.2 mM, and the pyrene solution was mixed with the HC NG at various concentrations of 0.001 to 1 mg/ml in a volume ratio of 1:1. An excitation spectrum (300 to 360 nm, emission at 390 nm) of the pyrene was obtained using a fluorescence spectrophotometer (F-7000, Hitachi High-Technologies Corporation, Tokyo, Japan), and the CMC was determined from intensities at 338 nm and 333 nm and a concentration ratio of the HC NG, and the CMC of the sample was calculated to be approximately 0.006 mg/ml (FIG. 5). Therefore, it was confirmed that the amphipathic property of the HC NG results from formation of a micelle consisting of hydrophobic cholesterol and hydrophilic HA in an aqueous solution.

Particle sizes of the synthesized HC NG and HC-BA NG were analyzed by dynamic light scattering (DLS). Specifically, HC NGs and HC-BA NGs (2 mg/mL) were dissolved in a PBS buffer (pH 7.4), and the solution was subjected to ultrasonication using a probe-type ultrasonicator (Branson, Mo., USA) for 2 minutes. Then, the sample was further purified using a membrane filter with a pore size of 0.45 mm, and analyzed using a DLS instrument (Zetasizer Nano ZS, Malvern, UK). Therefore, it was confirmed that the fluid dynamic sizes of the HC NG and the HC-BA NG are 250 nm or less (FIG. 6).

Afterward, the swelling characteristic of the HC-BA NG used in the present invention was analyzed. First, a sample was centrifuged at 3000 rpm for 10 minutes, and the precipitated pellet was dried in a vacuum oven for 12 hours. The dried pellet was directly measured using a microbalance, and the swelling characteristic was evaluated at a suitable time point in a physiological buffer. A hydrogel swelling ratio was measured using the weight of the HC-BA NG and calculated according to the following equation.

$$\text{Swelling ratio (\%)} = \frac{(\text{swollen weight} - \text{dried weight})}{\text{dried weight}} \times 100\% \quad [\text{Equation 1}]$$

As shown in FIG. 7A, the dried HC-BA NG rapidly absorbed water for 10 minutes, and after two hours, it was swelled up to 180% and saturated. Afterward, such an NG was immersed in 5, 10 and 20 mM glucose solutions (FIG. 7B), and it was confirmed that the swelling ratio increased up to 200 to 230% after 40 minutes of the immersion. A change in the size of the HC-BA NG nanoparticles was able to be identified by DLS analysis (FIG. 7C). In a glucose-free PBS buffer, the size of the HC-BA NG particles was approximately 300 nm, but after glucose was added to the PBS (final concentration: 100 Mm), it was confirmed that the particle size increased up to approximately 1 mm. In a control experiment, BA-free HC NG showed volume expansion (swelling) in PBS, but did not show a swelling difference in the presence of glucose (FIG. 7D). Such results prove that, as described above in the explanation of the swelling principle of the hydrogel, in the HC NG, a nonionic trigonal BA unit binds to a diol of the glucose, thereby becoming a negatively-charged tetrahedral boronate ester, and therefore, at a physiological pH, the hydrogel was swelled due to the electrostatic repulsion between the negatively-charged carboxyl group of the HA and an anionic boronate.

FIG. 8 shows a process of HC-BA NG formation (A), the morphology (TEM) of a HC-BA NG nanoparticle (B), and an SEM image of a yarn formed by twisting the HC-BA NG-embedded MWCNT (glucose-reactive hydrogel-based artificial muscle). Using cholesterol-bonded HA, a spherical nanoparticle (HC-NG) in which a hydrophilic backbone consisting of hydrophilic HA was present on the outside, and hydrophobic cholesterol was accumulated in the inside may be formed. Phenyl boronic acid, as a glucose sensing part, binds to NG (FIG. 8A). The surface morphology of the HC-BA NG was observed using a TEM microscope (Philips CM 200, CA, USA) after negative-staining with uracil acetate. According to the TEM image of FIG. 8B, it was confirmed that the HC-BA NG is a spherical nanoparticle with a diameter of 200 to 250 nm. As shown in the SEM image of FIG. 8C, it was confirmed that, under the same twisting conditions, the CNT yarn formed by twisting only the CNT sheet (bare MWCNT yarn) has a thickness of approximately 30 μm and a helix angle ($\alpha$) of approximately 20 degrees (°) (top of FIG. 8C), and an HC-BA NG-deposited yarn has a thickness of approximately 40 μm and a helix angle ($\alpha'$) of approximately 20 degrees (°) (bottom of FIG. 8C). In addition, according to such images, it was confirmed that the HC-BA NGs synthesized in the present invention were uniformly deposited without defects such as grain, strain and cracking.

Then, as a guest material according to the present invention, the twisting of the glucose-reactive hydrogel-based artificial muscle formed by twisting the HC-BA NG-embedded MWCNT sheet was evaluated. An experiment was performed with a PBS flow system of various glucose concentrations, which was provided using a peristaltic pump (LEAD-2, Baoding Longer Precision Pump Co., Ltd., Hebei, China) (FIG. 9). To confirm the twisting of the artificial muscle, the CNT yarn formed by twisting only the CNT sheet (bare MWCNT yarn) according to Preparation Example 3 and the glucose-reactive hydrogel-based artificial muscle formed by twisting the CNT sheet into a fiber type according to Preparation Example 2 were connected with a paddle having a size of 0.5×2.0 mm and fixed, each of the ends of the CNT yarn and the glucose-reactive hydrogel-based artificial muscle, which were not connected with a paddle, was fixed using a waterproof epoxy adhesive, and after overnight drying, forming a glucose-reactive, rotary artificial muscle was formed (FIG. 1). Subsequently, to stabilize a rotation angle of the driven yarn, the artificial muscle was immersed in a PBS buffer for 2 hours. At various glucose concentrations (0, 5, 10, and 20 Mm), the PBS buffer was injected into each system for 20 minutes. Afterward, a glucose-free PBS buffer was reinjected into the sample for 30 minutes. In an experiment of continuous concentration variation of glucose, an interval of the exchange of a solution was 30 minutes, and a rotation angle of the artificial muscle was indicated.

Accordingly, it was confirmed that the reversible paddle rotation in the PBS buffer depends on a glucose concentration in the buffer resulting in the swelling/shrinkage of the HC-BA NGs in the yarn. As shown in FIG. 10A, it was confirmed that the measured rotation angle (measured as a degree of paddle rotation per yarn length (mm)) varied from approximately 10°/mm (at 10 mM glucose) to 40°/mm (at 100 mM glucose), and the paddle rotation angle returned to the initial position when glucose was removed. After the glucose-containing buffer was added, the paddle was rotated in an untwisting direction to drive the yarn, and after 20 minutes, the rotation of the paddle was stopped. When the glucose-containing buffer was replaced with a glucose-free buffer, the rotation direction of the paddle was reversed, and the final rotation angle was obtained in approximately 30 minutes. Such a result infers that the glucose-reactive artificial muscle according to the present invention can be effectively used as a self-driven, reversible glucose sensor with a short reaction time.

FIG. 10B shows a graph of a paddle rotation angle according to a glucose concentration. Accordingly, it can be confirmed that, when the glucose concentration ranges from 5 to 20 mM, the rotation angle linearly increases from 0 to 20 degrees (°). This shows that the twisting angle of the artificial muscle according to the present invention accurately responds to the concentration of glucose required to monitor a normal glucose level (before meal: 5.6 mM, 2 hrs after meal: 7.8 mM) and an abnormal glucose level (before meal: 7.0 mM or more, 2 hrs after meal: 11.1 mM or more) in a human. Therefore, this result infers that the glucose sensitivity of the artificial muscle according to the present invention can be effectively applied to drug delivery devices that can regulate drug delivery by twisting.

As a result, it was confirmed that the glucose-reactive artificial muscle according to the present invention formed by twisting the MTCNT sheet in which HC-BA NG, which is a guest material, was embedded can be reversibly twisted in sensitive response to glucose with various concentrations. Accordingly, the artificial muscle according to the present invention can used as an implantable, self-driven sensor for regulating drug delivery. Further, the present invention can be effectively applied to a variety of medical devices such as drug delivery systems, BioMems, in vivo nano- and micromachines, smart scaffolds for tissue engineering, drug injection channel opening/closing devices that are regulated according to blood sugar, drug injection concentration regulatory devices, nerve stimulators, etc., and nanomedical, drug delivery, rehabilitation medical and bioengineering fields.

The invention claimed is:

1. A glucose-reactive hydrogel-based artificial muscle, comprising:
   a multi-layered carbon nanotube (CNT) sheet; and
   hydrogels embedded in the surface of the CNT sheet,
   wherein the artificial muscle is a fiber in which the hydrogel-embedded CNT sheet is twisted, and
   the hydrogel has a reversible volume change by the reaction with glucose.

2. The artificial muscle according to claim 1, wherein the artificial muscle has a twisted or coiled structure.

3. The artificial muscle according to claim 1, wherein the hydrogels are boronic acid-conjugated hyaluronic acid/cholesterol nanogels, represented by Formula 1 below:

[Formula 1]

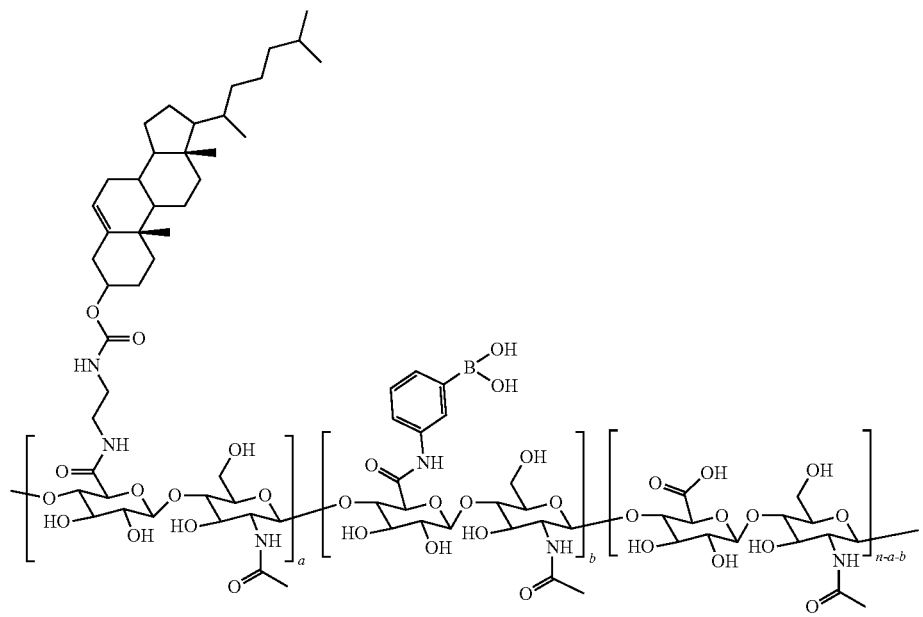

wherein n is an integer of 2 to 20000, and each of a and b is an integer of 1 to 10000.

4. The artificial muscle according to claim 1, wherein the hydrogels are embedded at a content of 80 to 99 wt % with respect to the total content of the hydrogel-embedded CNT sheet.

5. The artificial muscle according to claim 1, wherein the glucose concentration ranges from 1 to 100 mM.

6. A glucose-reactive, rotary artificial muscle, comprising:
a fiber-type artificial muscle unit including the glucose-reactive hydrogel-based artificial muscle according claim 1; and
a fiber-type scaffold unit formed by twisting a multi-layered CNT sheet, wherein one end of the fiber-type artificial muscle unit is connected with one end of the fiber-type scaffold unit by a paddle, and
the other end of the fiber-type artificial muscle unit and the other end of the fiber-type scaffold unit are each independently fixed using fixing devices.

7. The rotary artificial muscle according to claim 6, wherein the fiber-type artificial muscle unit and the fiber-type scaffold unit are twisted in the same twisting direction so as to have a twisted or coiled structure.

8. The rotary artificial muscle according to claim 6, wherein the fiber-type artificial muscle unit is reversibly expanded or shrunk in volume by the reaction with glucose in such a manner that the fiber-type scaffold unit is rotated.

* * * * *